US 8,844,524 B2

(12) United States Patent
Kwok

(10) Patent No.: US 8,844,524 B2
(45) Date of Patent: *Sep. 30, 2014

(54) CPAP MASK AND SYSTEM

(71) Applicant: ResMed Limited, Bella Vista (AU)

(72) Inventor: Philip Rodney Kwok, Chatswood (AU)

(73) Assignee: ResMed Limited, Bella Vista (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/749,735

(22) Filed: Jan. 25, 2013

(65) Prior Publication Data

US 2013/0133661 A1    May 30, 2013

Related U.S. Application Data

(60) Continuation of application No. 12/652,792, filed on Jan. 6, 2010, now Pat. No. 8,375,944, which is a division of application No. 10/572,813, filed as application No. PCT/AU2004/001309 on Sep. 24, 2004, now Pat. No. 7,913,692.

(60) Provisional application No. 60/505,718, filed on Sep. 25, 2003.

(30) Foreign Application Priority Data

Sep. 24, 2004   (WO) ................ PCT/AU2004/001309

(51) Int. Cl.
    *A61M 11/00*      (2006.01)

(52) U.S. Cl.
    USPC ................................. 128/204.18; 128/204.23

(58) Field of Classification Search
USPC ............ 128/201.22–201.28, 201.19, 206.19, 128/206.17, 205.25, 205.24, 205.27, 128/205.29, 206.12, 206.21, 206.24, 128/206.28, 207.11, 207.12, 204.18–204.26
See application file for complete search history.

(56) References Cited

U.S. PATENT DOCUMENTS

| | | |
|---|---|---|
| 4,233,972 A | 11/1980 | Hauff et al. |
| 4,297,999 A | 11/1981 | Kitrell |
| 4,590,951 A | 5/1986 | O'Connor |
| 5,154,168 A | 10/1992 | Schlobohm |
| 5,303,701 A | 4/1994 | Heins et al. |
| 5,318,020 A | 6/1994 | Schegerin |
| 5,372,130 A | 12/1994 | Stern et al. |
| 5,394,870 A | 3/1995 | Johansson |
| 5,517,986 A | 5/1996 | Starr et al. |
| 5,577,496 A | 11/1996 | Blackwood et al. |

(Continued)

FOREIGN PATENT DOCUMENTS

| | | |
|---|---|---|
| CN | 2277785 Y | 4/1998 |
| CN | 101816814 B | 11/2012 |

(Continued)

OTHER PUBLICATIONS

Notification of the First Office Action mailed Sep. 3, 2013 in Chinese Application No. 201110303746.6, with English translation (13 pages).

(Continued)

*Primary Examiner* — Steven Douglas
(74) *Attorney, Agent, or Firm* — Nixon & Vanderhye P.C.

(57) ABSTRACT

A continuous positive air pressure ("CPAP") or ventilator system includes a mask and an air flow generator. The air flow generator is mounted or provided to the mask's wearer. In one embodiment, air flow generator is mounted on the mask.

26 Claims, 14 Drawing Sheets

(56) References Cited

U.S. PATENT DOCUMENTS

| | | |
|---|---|---|
| 5,884,624 A | 3/1999 | Barnett et al. |
| 6,050,262 A | 4/2000 | Jay |
| 6,213,119 B1 | 4/2001 | Brydon et al. |
| 6,435,184 B1 | 8/2002 | Ho |
| 6,513,526 B2 | 2/2003 | Kwok et al. |
| 6,561,190 B1 | 5/2003 | Kwok |
| 6,561,191 B1 | 5/2003 | Kwok |
| 6,772,760 B2 | 8/2004 | Frater et al. |
| 6,772,762 B2 | 8/2004 | Piesinger |
| 7,069,932 B2 | 7/2006 | Eaton et al. |
| 7,178,525 B2 | 2/2007 | Matula et al. |
| 7,255,103 B2 | 8/2007 | Bassin |
| 7,681,575 B2 | 3/2010 | Wixey et al. |
| 2002/0029777 A1 | 3/2002 | Zimprich et al. |
| 2003/0062045 A1 | 4/2003 | Woodring et al. |
| 2003/0089372 A1 | 5/2003 | Frater et al. |
| 2003/0154983 A1 | 8/2003 | Marx |
| 2003/0172930 A1 | 9/2003 | Kullik et al. |
| 2004/0079373 A1 | 4/2004 | Mukaiyama et al. |
| 2005/0034724 A1 | 2/2005 | O'Dea |
| 2006/0096596 A1 | 5/2006 | Occhialini et al. |
| 2006/0150973 A1 | 7/2006 | Chalvignac |
| 2007/0000493 A1 | 1/2007 | Cox |
| 2008/0304986 A1 | 12/2008 | Kenyon et al. |
| 2010/0108070 A1 | 5/2010 | Kwok |

FOREIGN PATENT DOCUMENTS

| | | |
|---|---|---|
| DE | 10 261 602 | 7/2004 |
| EP | 0 066 451 | 8/1985 |
| EP | 0 164 946 | 12/1985 |
| EP | 0 528 733 | 9/1996 |
| EP | 1 318 307 A1 | 6/2003 |
| GB | 2 099 709 A | 12/1982 |
| GB | 2 141 348 A | 12/1984 |
| GB | 2 209 474 A | 5/1989 |
| GB | 2 215 216 | 9/1989 |
| JP | 58-29468 A | 2/1983 |
| JP | 60-68869 A | 4/1985 |
| JP | 2003-117013 A | 4/2003 |
| WO | WO 99/13931 | 3/1999 |
| WO | WO 01/94466 A1 | 12/2001 |
| WO | WO 02/02169 A1 | 1/2002 |
| WO | WO 02/45784 A1 | 6/2002 |
| WO | WO 2005/028009 A1 | 3/2005 |
| WO | WO 2007/048205 A1 | 5/2007 |
| WO | WO 2007/117716 A2 | 10/2007 |
| WO | WO 2007/124108 A2 | 11/2007 |
| WO | WO 2008/028247 A1 | 3/2008 |
| WO | WO 2008/108789 A1 | 9/2008 |

OTHER PUBLICATIONS

Decision of Rejection mailed Aug. 27, 2013 in Japanese Application No. 2011-115647, with English translation (4 pages).
International Search Report for PCT/AU2004/001309 dated Oct. 22, 2004.
Chinese Office Action and English Translation for corresponding Chinese Application No. 200480028014.9, issued Oct. 24, 2008, 15 pages.
Extended European Search Report mailed May 20, 2009 in European Application No. 09001343.4.
U.S. Appl. No. 60/494,119, filed Aug. 2003, Gunaratnam et al.
Notice of Reasons for Rejection mailed Jan. 5, 2010 in Japanese Application No. 2006-527225, with English translation.
Decision of Rejection Mailed Feb. 15, 2011 in Japanese Application No. 2006-527225, with English Translation (4 pages).
Notification of First Office Action Issued Mar. 8, 2011 in Chinese Application No. 201010154188.7, with English translation.
Appeal Decision issued Sep. 4, 2012 in Japanese Appeal No. 2011-10866, with partial English translation (20 pages).
JSME Mechanical Engineers' Handbook, New 6$^{th}$ Edition printed Jul. 30, 1993, Japan Society of Mechanical Engineers, p. 115 of B5, vol. 3, Chapter 1, General Air Devices and Fig. 268, with English Translation (6 pages).
Notice of Reasons for Rejection issued Nov. 13, 2012 in Japanese Application No. 2011-115647, with English translation (4 pages).
Notification of Acceptance of the Request for Invalidation issued Nov. 29, 2013 in Chinese Patent No. 201010154188.7, with English Translation (3 pages).
Request for the Invalidation of a Patent Right mailed Sep. 30, 2013 in Chinese Patent No. 201010154188.7, with English Translation (130 pages).
Second Office Action mailed May 22, 2014 in Chinese Application No. 201110303746.6 (13 pp.).

CPAP MASK AND SYSTEM

CROSS-REFERENCES TO RELATED APPLICATIONS

This application is a continuation of U.S. application Ser. No. 12/652,792, filed Jan. 6, 2010, now U.S. Pat. No. 8,375,944, which is a divisional of U.S. application Ser. No. 10/572,813, filed Apr. 17, 2006, now U.S. Pat. No. 7,913,692, which is the U.S. national phase of international application number PCT/AU2004/001309 filed Sep. 24, 2004, which designated the U.S. and claims priority to U.S. Provisional Application No. 60/505,718 filed Sep. 25, 2003, the entire contents of each of which are hereby incorporated by reference.

BACKGROUND OF THE INVENTION

1. Field of the Invention

The present invention relates to ventilators, e.g., continuous positive air pressure ("CPAP") systems comprising a mask and an air flow generator, wherein the air flow generator is mountable to the mask's wearer. In one embodiment, the present invention provides CPAP systems wherein an air flow generator is mounted on the mask. In other embodiments, the air flow generator may be provided to the body of the wearer, e.g., the arm, leg, chest or waist, and a short air delivery tube can be used to connect the mask with the air flow generator.

2. Description of Related Art

CPAP administration is commonly used to treat respiratory conditions such as obstructive sleep apnea. The procedure for CPAP administration typically involves sealingly engaging a mask over a patient's nasal and/or oral region and supplying pressurized air to a chamber formed by the interior of the mask. In conventional systems, the air is supplied to the mask by an air flow generator typically placed in proximity to the patient's bed. An air delivery tube is thus needed to deliver air generated by the air flow generator to the mask.

There are two main sources of instability of a mask system during use or sleep. Normal patient movement can create instability, for example, a patient rolling on his or her side, which may cause the mask to interfere with the bedding material. Another concern of using an air delivery tube that is connected to an apparatus away from the patient is so-called "tubing drag", which refers to a drag force on the air delivery tube which is draped over the back or side of the bed. Tubing drag can be created or complicated by movement of the wearer. Tubing drag may cause relative movement between the mask seal and the patient's face during the CPAP administration and produce leaks and/or discomfort.

Another concern involving the air delivery tube is the length thereof (often about 2 meters or more), which may impart a lag in the response and rise times in delivering pressured air from the air flow generator to the mask. Increased flow impedance and/or pressure drop due to diameter and length of tubing may also necessitate a larger blower motor to compensate for the pressure drop along the air delivery tube.

U.S. Pat. Nos. 4,590,951; 5,372,130; and 6,435,184 describe masks for safety applications.

SUMMARY OF THE INVENTION

Aspects of the present invention include addressing the concerns in the art, e.g., by reducing or eliminating the risk of tubing drag during CPAP administration.

A further aspect of the present invention is to provide the wearer with a greater freedom of movement in bed without compromising seal and/or comfort.

Another aspect of the present invention includes reducing or eliminating the lag in response/rise times in delivering pressured air from the generator to the mask.

In one embodiment, a ventilator or CPAP system comprises a mask and an air flow generator, wherein both the mask and the air flow generator are provided to or on the wearer. In one embodiment, the mask is configured to be fitted to the patient's face and the air flow generator is mountable to the wearer's body. The air flow generator may be provided directly to the mask.

According to one embodiment a CPAP system comprises a face mask and an air flow generator, wherein the air flow generator is mounted on the face mask.

In a further embodiment, a ventilator or CPAP system comprises:

(i) a face mask configured to be placed over an area of a wearer's face, the face mask having:
  (1) a shell;
  (2) a cushion provided to a perimeter of the shell to sealingly connect the face mask to the area of a wearer's face and thereby form a chamber between the shell and the wearer's face; and
  (3) an inlet port in the shell to receive a flow of breathable gas;
(ii) an air flow generator, said air flow generator being mounted on said mask and being capable of creating a pressure of about 2-40 cm $H_2O$ in the chamber.

In embodiments, a ventilator or CPAP system includes an air flow generator able to be located sufficiently close to a wearer so that an air delivery tube may be less than 1.5 meters in length.

In one embodiment, a ventilator or CPAP system comprises:
  a face mask having an inlet port,
  an air flow generator having an outlet, and
  at least one air delivery tube for delivering breathable gas from the gas outlet to the inlet port,
  wherein the at least one air delivery tube does not exceed about 1.5 meters in length. The at least one air delivery tube may include two or more air delivery tubes having a combined overall length of not more than about 1.5 meters.

In a further embodiment, a ventilator or CPAP system comprises:
(i) a face mask having
  (1) a shell;
  (2) a cushion provided to the shell to sealingly connect the face mask to a wearer's face and thereby form a chamber between the shell and the wearer's face, and;
  (3) an air inlet port in the shell to receive a flow of breathable gas;
(ii) an air flow generator; and
(iii) an air delivery tube not exceeding 1.5 meters in length, the air delivery tube being functionally connected to the air inlet port and the air flow generator to create a pressure of about 2-40 cm $H_2O$ in the chamber by delivery of breathable gas from the air flow generator to the air inlet port.

Additional aspects, advantages and features of the present invention are set forth in this specification, and in part will become apparent to those skilled in the art on examination of the following, or may be learned by practice of the invention. The inventions disclosed in this application are not limited to any particular set of or combination of aspects, advantages and features. It is contemplated that various combinations of

DETAILED DESCRIPTION OF THE INVENTION

A CPAP system includes a mask and an air flow generator, wherein the air flow generator is provided to a wearer of the mask. In one embodiment, the air flow generator is mountable to a wearer's body (including a wearer's clothing). In another embodiment, the air flow generator is mounted on or provided to the mask.

FIGS. 1-11B show several embodiments of CPAP systems according to the present invention.

Figure 1:
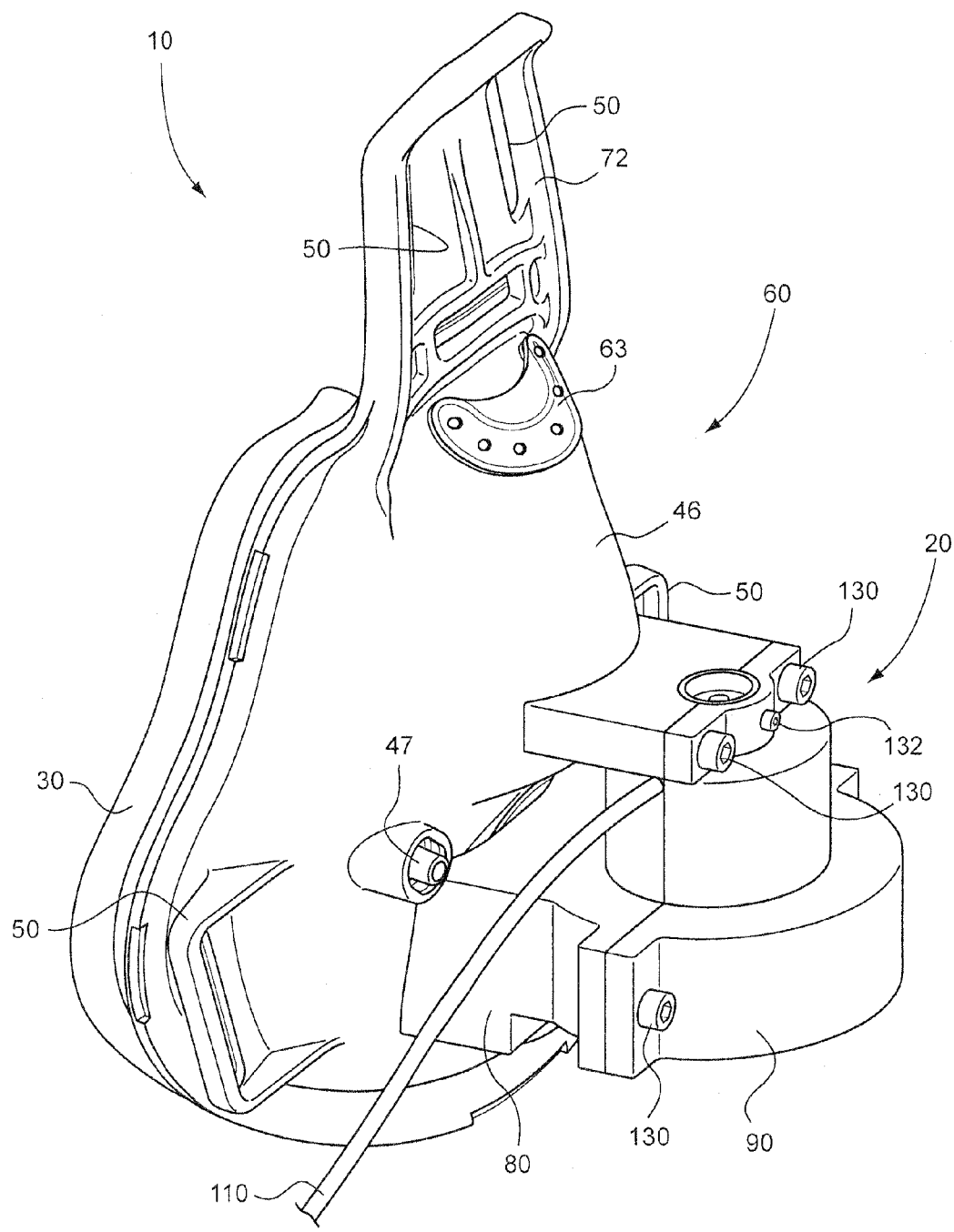
FIG. 1 is a perspective view of a CPAP system according to one embodiment of the invention.

Referring to FIG. 1, a CPAP system 10 includes a mask 60 provided with a cushion 30 and a shell 46 to form an air chamber in communication with the airways of a wearer. In this example, the mask 60 covers at least the oral and nasal region of a wearer. However, the mask 60 could also be a nasal mask and cover, for instance, only the nasal region or only the mouth region. In either case, it is preferable that the mask does not cover or interfere with the wearer's eyes or vision. The mask may include a vent opening 61 for $CO_2$ gas washout, and one or more inlet ports 47 for use in introducing supplemental gas, e.g., oxygen, into the air chamber. The vent opening 61 can be covered with a suitable insert 63 or the like to controllably exhaust $CO_2$. The insert is described in ResMed's U.S. Pat. Nos. 6,561,190 and 6,561,191, each incorporated herein by reference in its entirety.

Mask cushion 30 is preferably made of a soft material (e.g. a rubber material, such as a silicone elastomer) and sealingly connects to the wearer's face to form the air chamber between the wearer's face and the mask 60. The shell can be made of a relatively hard plastic, although the shell can be made of the same material as the cushion 30, in some applications. Examples of cushions 30 are described in, for instance, U.S. Pat. No. 6,513,526, assigned to ResMed Limited, which is hereby incorporated in its entirety by reference. Commercial examples of mask 60 include, for instance, the Mirage® Full Face Mask Series II from ResMed Limited (not taking into account adjustments described below in more detail).

Headgear connectors 50 are provided to the shell 46. Headgear connectors are designed to receive headgear straps for securing CPAP system 10 to a wearer's head (securing straps 55 are shown in FIGS. 9 and 10A). Attached to shell 46 is an extension 72 which will generally be provided with a resilient pad (not shown) to engage the forehead of the wearer, to provide additional stability. A strap may be provided to each connector 50 of the extension 72 for contact with the wearer's crown. Alternatively, or in addition, a strap connector 50a may be provided to the extension 72 such that the strap extends over the top of the wearer's head, as shown in FIGS. 9 and 10A.

The air chamber formed between a wearer's face and the interior of mask 60 receives breathable gas (e.g. air) through air inlet port 56 (see FIG. 2), which is designed to be placed in close proximity to (e.g. over) the wearer's oral/nasal region. The breathable gas is supplied by air flow generator 20. In one embodiment, the air flow supplied by air flow generator 20 creates single or variable pressures within the air chamber in the range of 2-40 cm $H_2O$, for instance 10-28 cm $H_2O$ or 15-20 cm $H_2O$; or relatively constant 10 cm $H_2O$ etc.

Figure 2:
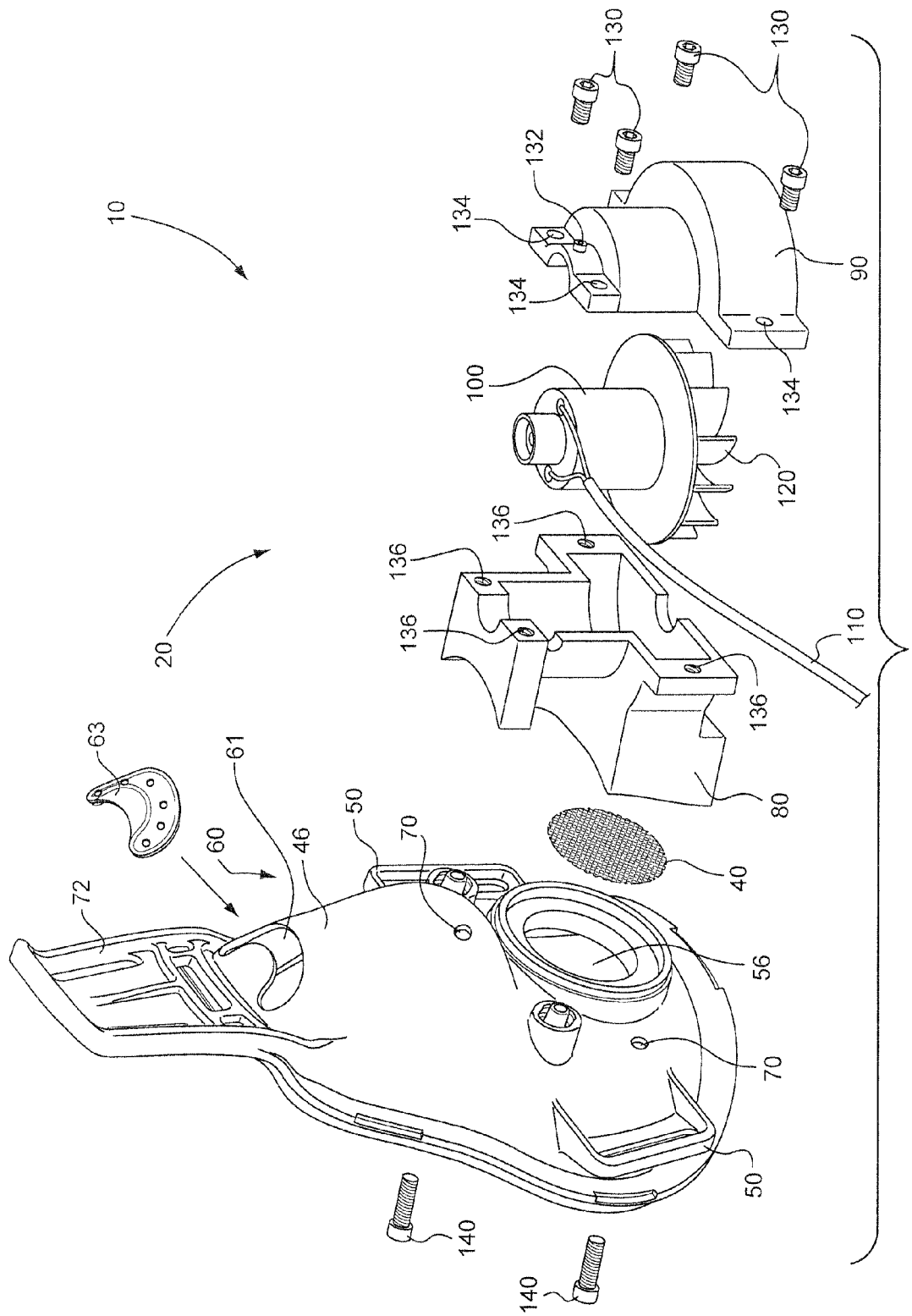
FIG. 2 is an exploded view of the CPAP system of FIG. 1.
Figure 3:
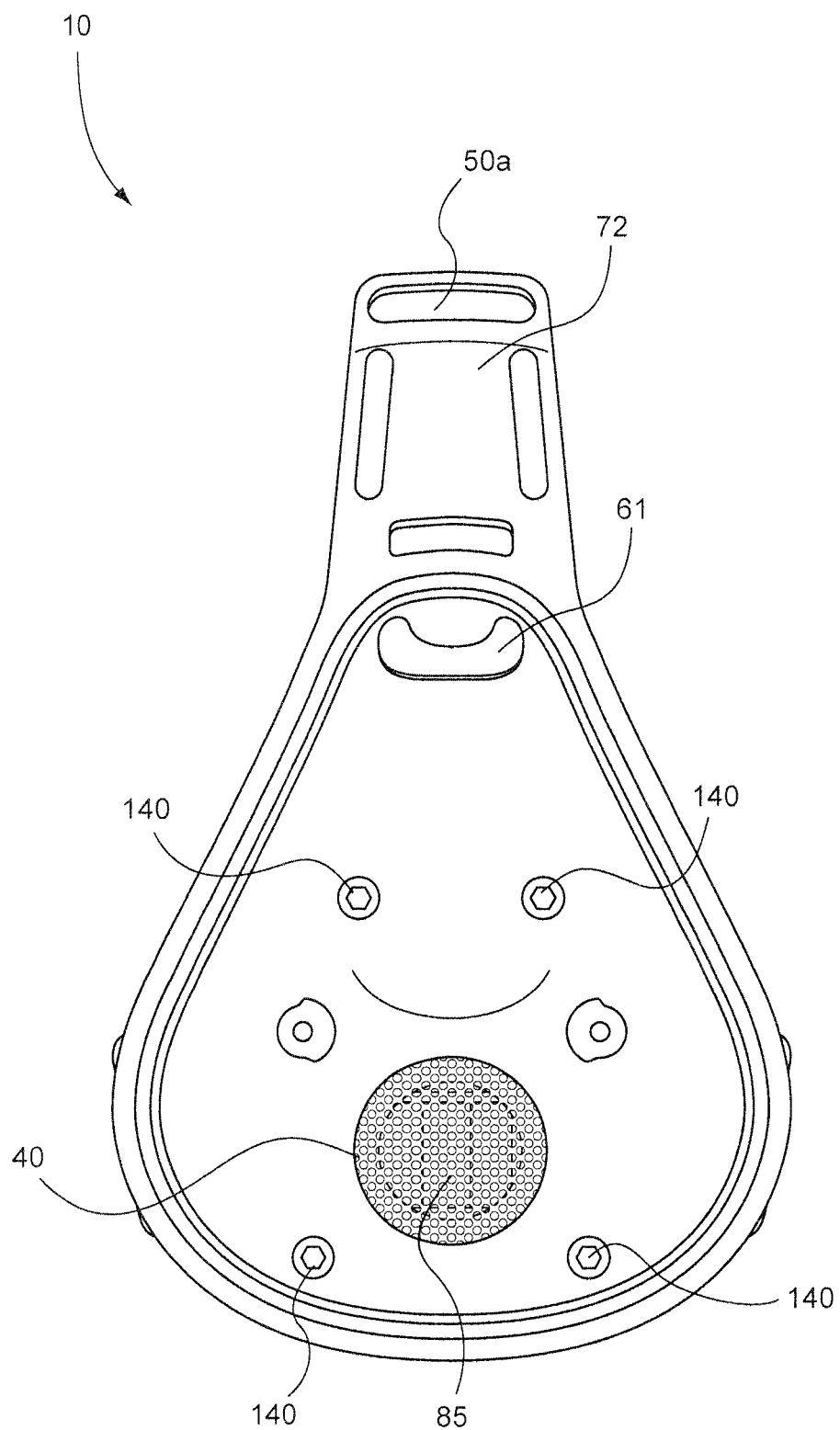
FIG. 3 is a front view taken from an interior of the CPAP system of FIG. 1.
Figure 4:
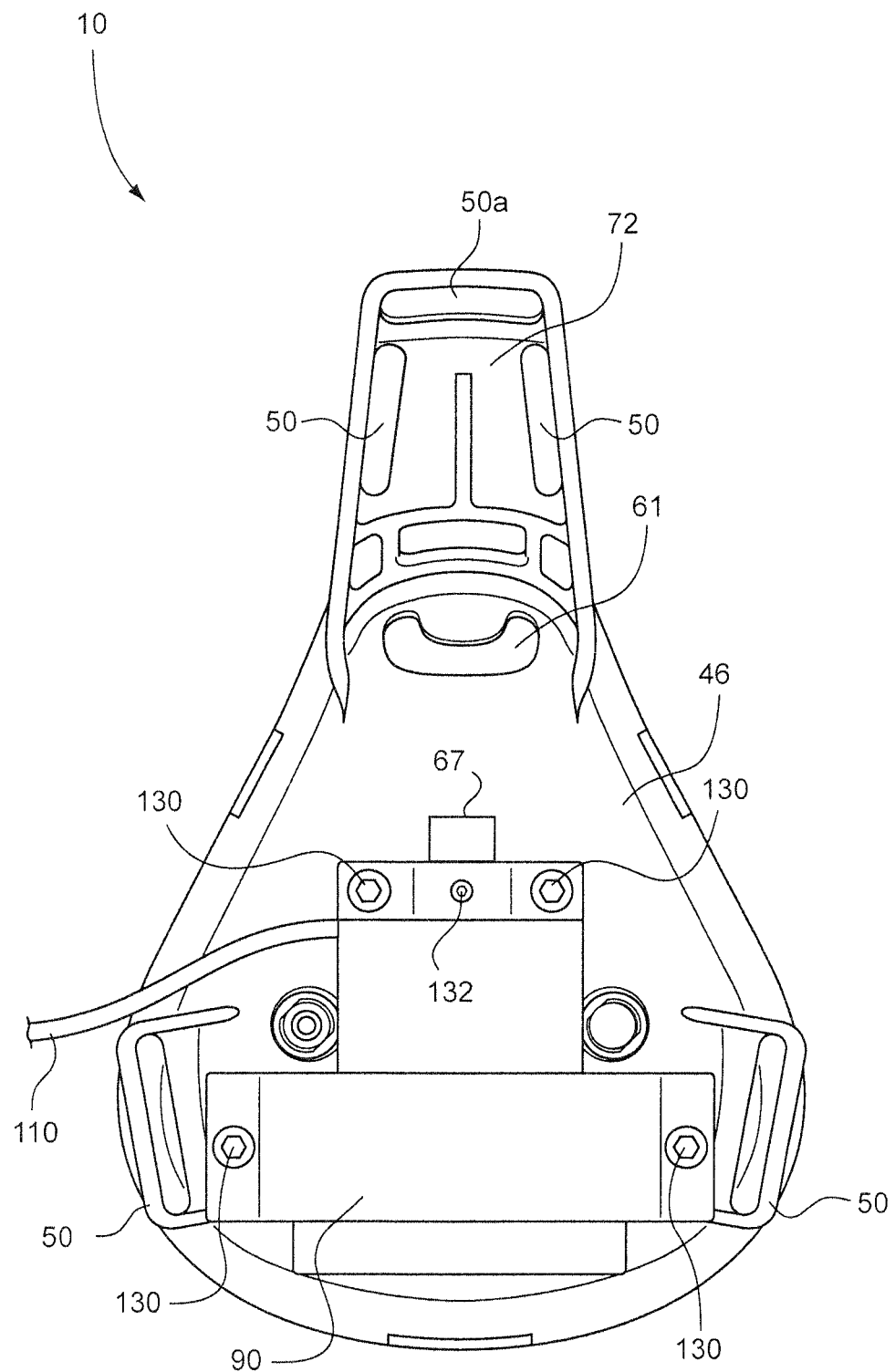
FIG. 4 is a rear view taken from an exterior of the CPAP system of FIG. 1.
Figure 5:
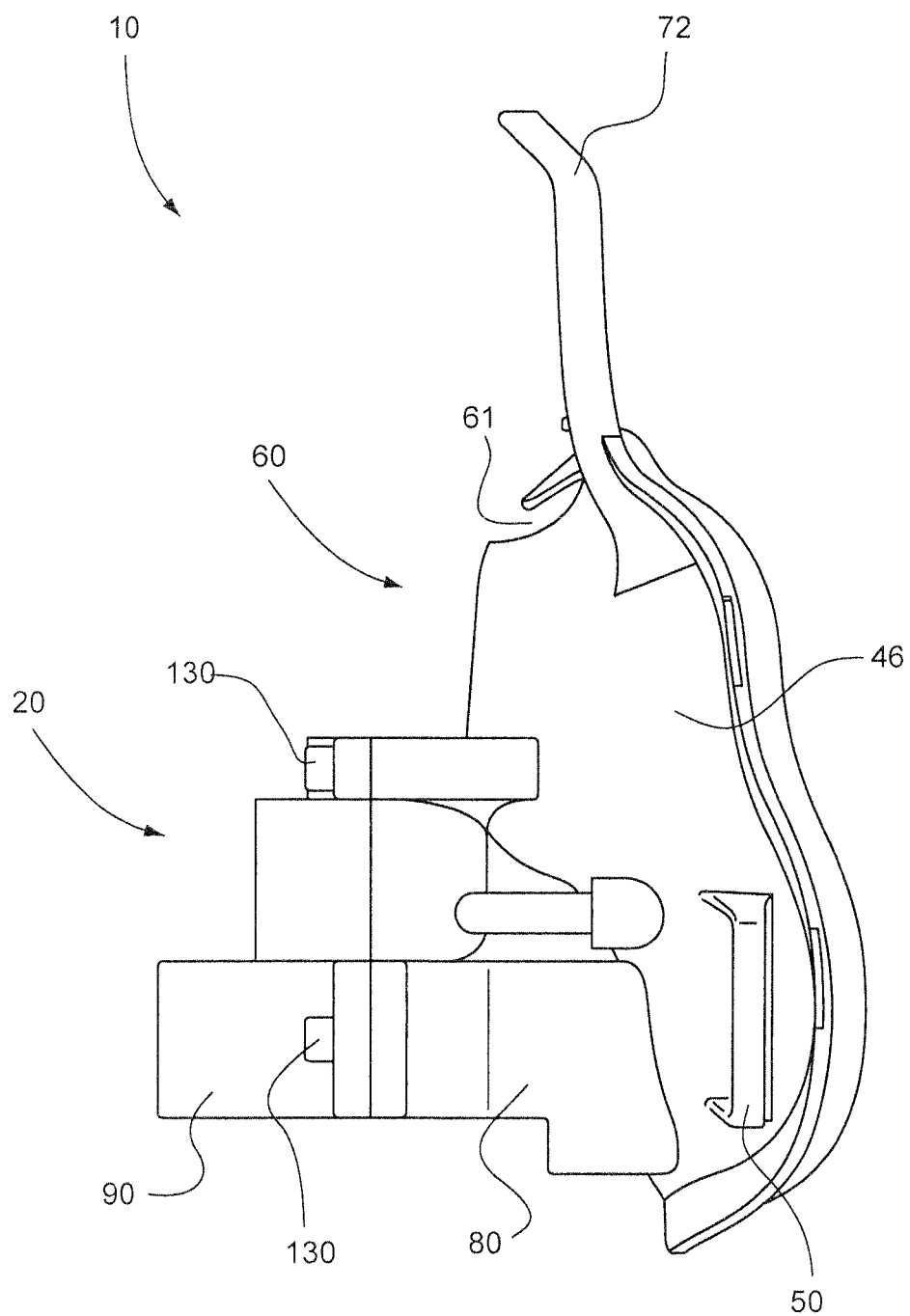
FIG. 5 is a right side view of the CPAP system of FIG. 4.
Figure 6:
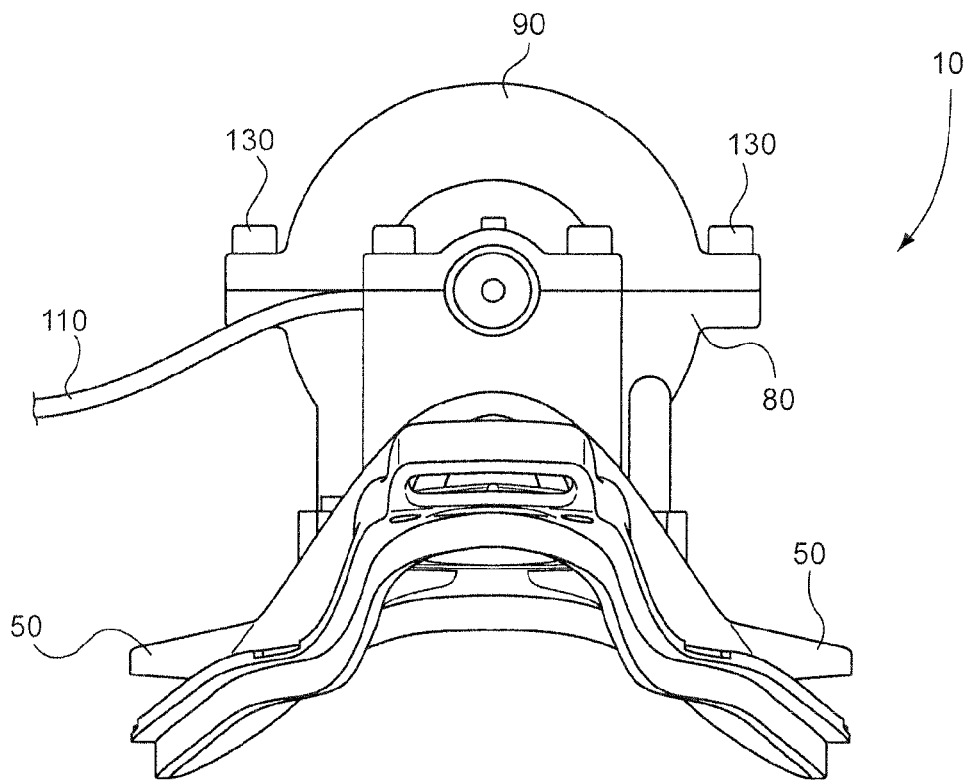
FIG. 6 is a top view of the CPAP system of FIG. 4.
Figure 7:
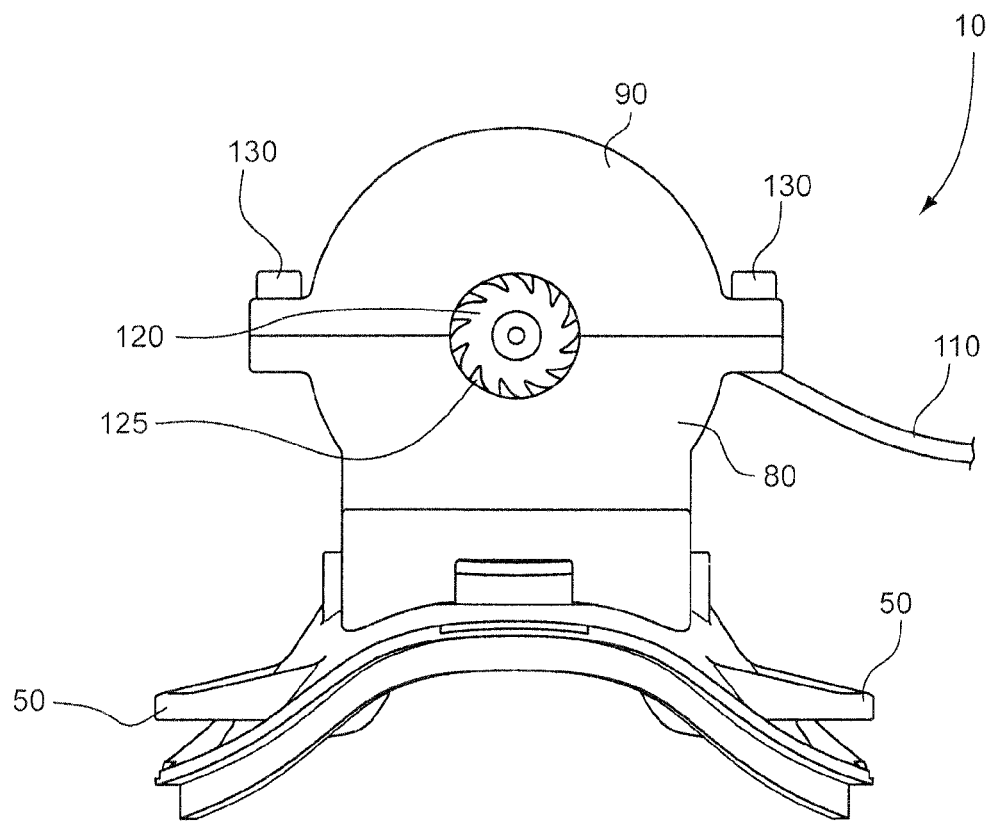
FIG. 7 is a bottom view of the CPAP system of FIG. 4.

Referring to FIG. 2, air flow generator 20 includes, for example, a first part 90 and a second part 80 that are joined, e.g., by screws 130 through bores 134 and 136 to form a housing for impeller 120 and motor 100. The parts 80 and 90 may be made from a variety of materials, for instance from cured resinous materials, from metal (e.g. aluminum), or from polymers, e.g. from polyolefins (such as polyethylene or polypropylene), polycarbonates, or acrylonitrile-butadiene-styrene polymers ("ABS").

Motor 100 drives impeller 120. Power is supplied to motor 100 via power cord 110 and the motor is fixedly secured within the impeller housing by tightening screw 132. Examples of electrical motors include, for instance, miniature bullet motors commercially available from, e.g., Servo Magnetics Inc., of California. However, various types of motors may be used, including for instance pneumatic air powered motors in which case the energy source would be a tiny air line instead of an electrical pulse. The motor assembly may include multiple motors or single motors with multiple impellers, double ended impellers, etc. Other possibilities include separate systems which can deliver prescribed air pressure. In another variant, another motor impeller assembly can be utilized to modify, for instance, if an inflatable cuff is provided to react to stimulus or sensed parameters like leak problems. A separate motor impeller can be used to control positioning of the mask relative to the face or the profile of the cushion seal.

Examples of impellers include, for instance, the S6 CPAP impeller from ResMed Limited. Various impellers may be used, however, such as axial fans, radial fans, centrifugal fans, etc. or any new technology able to deliver the required flow of gas such as air.

The power cord 110 may receive power from any suitable power source, e.g., a wall power outlet, wall mounted transformers, a battery pack or other power storage medium. In one embodiment, power cord 110 includes sensor cables to register and/or adjust to data received from sensors that may be provided in the mask (e.g. $CO_2$, $O_2$, humidity, pressure, flow, and/or temperature sensors). In one embodiment, the monitoring of sensors occurs via infrared technology or radio waves. A control box may be provided to adjust, e.g., the motor speed, e.g., for bi-level treatment, or other parameters relative to the information received through the sensors.

Other embodiments may be to sense leak and adjust motor speed and thus delivery pressure or flow accordingly.

The power cord 110 can be connected to a small controller chip (not shown) integrated with an electrical transformer plugged into a power outlet. This provides greater flexibility, freedom of movement of the wearer, increased versatility during traveling, etc. Also, there are less components at the mask interface, less overall size of the system and potentially greater stability. The system may be used for bi-level treatment or general ventilatory applications, e.g., where the magnitude of the pressurized air varies. The system may also provide faster response and rise times and eliminate or at least reduce lag associated with air delivery tubes typically having a length of 2 m or more. The system may be easier to use from the perspective of a physician, a dealer or clinician, in that only one rather than numerous components need to be fitted for the wearer.

Another embodiment provides the ability to change the strap adjusting points; the ability to modify the fit of the mask relative to the face through the integrated sensing. For example, if there is a leak generated by the mask and a sensor, e.g., a pressure transducer 67 (FIG. 4), produces a signal indicative of leaking in the mask, the flow generator pressure could be modified. There is also an embodiment where bladders or cuffs or sections of the mask seal could be modified so that the seal profile is modified in certain regions until the leak is resolved and the sensors would provide feedback to the control box that the leak is gone and the motor can be controlled to react to the feedback. See, e.g., U.S. Pat. No. 6,772, 760, to ResMed, incorporated herein by reference in its entirety.

Sensing flow or pressure of the mask system will increase reaction time and having a motor and an impeller assembly mounted directly into a mask system would mean that reaction times to pressure and flow changes would be very rapid; therefore there is improved synchrony of delivered gas to the wearer. Presently, flow generators essentially need to predict when a patient is about to breathe in or have some delay or lag, for example, by pressure sensors mounted to the flow generator. By contrast, one aspect of the present embodiment allows the mask system to react very quickly, which provides excellent synchrony of the flow to a patient and this is key to treat patients especially those with respiratory insufficiency who require very good synchrony of flow generator flow pattern to a breathing patient.

Air flow generator 20, e.g., second part 80, is mounted on mask 60, e.g., with four screws 140 (only two are shown in FIG. 2) which extend through holes 70 (also, only two shown) into bores 136 (at the opposite side of screws 130). Of course, a variety of other methods for mounting the air flow generator 20 on full face mask 60 are feasible, such as using adhesives, using melt-welding, or integrally forming the shell 46 and second part 80 through injection molding. Still another embodiment includes the ability to easily remove the generator 20 from the mask, e.g., to facilitate cleaning, etc. One or more quick release clips could be used for this purpose.

In one embodiment, such as the embodiment shown in FIG. 2, a perforated screen 40 (e.g. a perforated metal screen, for instance a perforated aluminum screen) is placed between inlet port 56 and air flow generator 20. The screen separates the outlet 85 (FIG. 3) from air flow generator 20 and prevents foreign matter that might enter the air flow generator from reaching the wearer's oral and facial region (air outlet 85 is visible in FIG. 3 through screen 40). Perforated screen 40 also ensures that a wearer's tongue or other body parts larger than perforation size cannot contact the impeller 120. Examples of perforated screen 40 include, for instance, a mesh structure or a thin plate with a plurality of small bores. This arrangement also prevents any motor or impeller failure such as breakage from harming the wearer.

Figure 8:
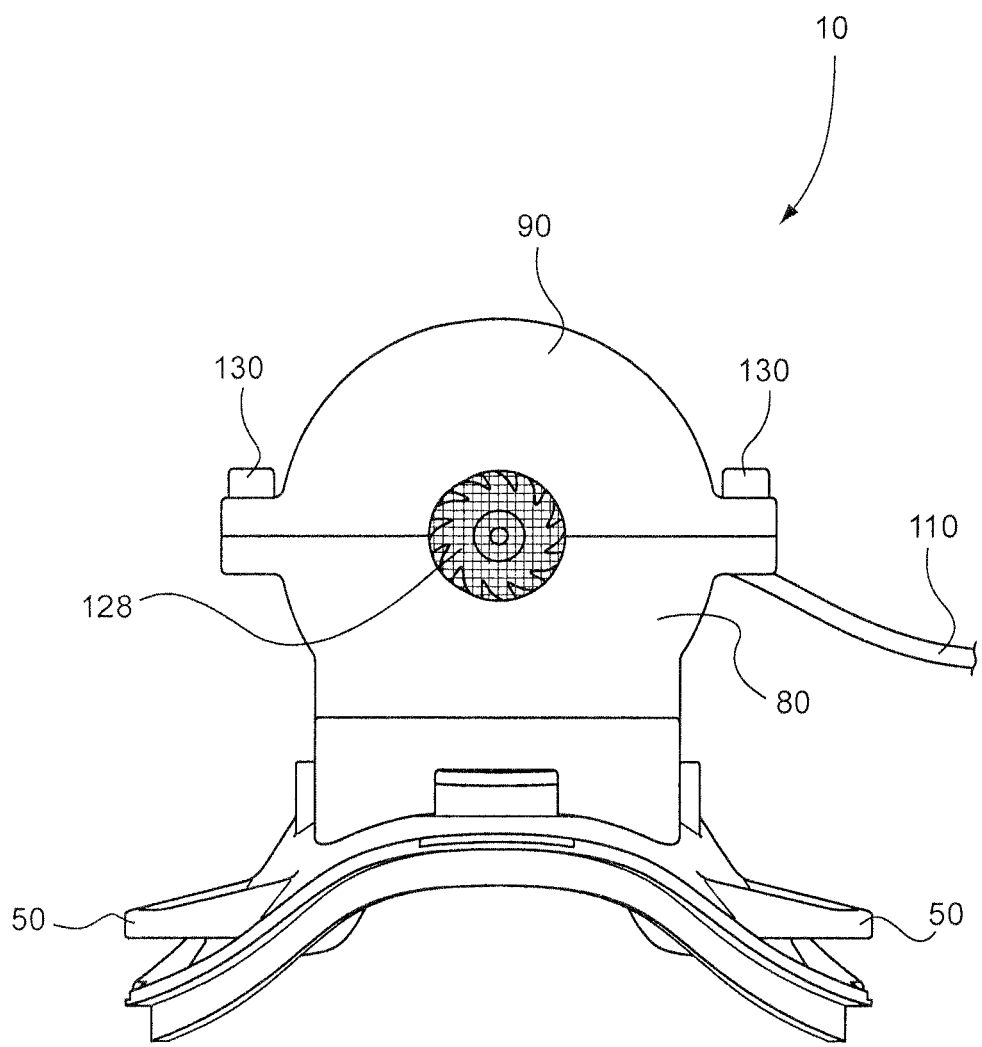
FIG. 8 is a bottom view of a CPAP system according to a further embodiment of the invention.

FIGS. 3-7 show various views for the CPAP mask 10 in FIGS. 1 and 2. A further embodiment is depicted in FIG. 8, where a filter 128 is provided in front of air intake opening 125 (See FIG. 7 for air intake opening 125). The filter 128 may be, for instance, a filter to prevent dust from entering the impeller system (i.e. a dust filter) or a perforated screen. Although a perforated screen does not prevent dust from entering the impeller system, it is helpful in avoiding, for instance, the wearer's fingers from being able to come into contact with the impeller 120. In addition, a perforated screen prevents larger particles from entering the impeller system. In one embodiment, the CPAP system and/or the air flow generator has a dust or antimicrobial filter. In a further embodiment, the CPAP system and/or air flow generator is absent a dust or antimicrobial filter.

Figure 9A:
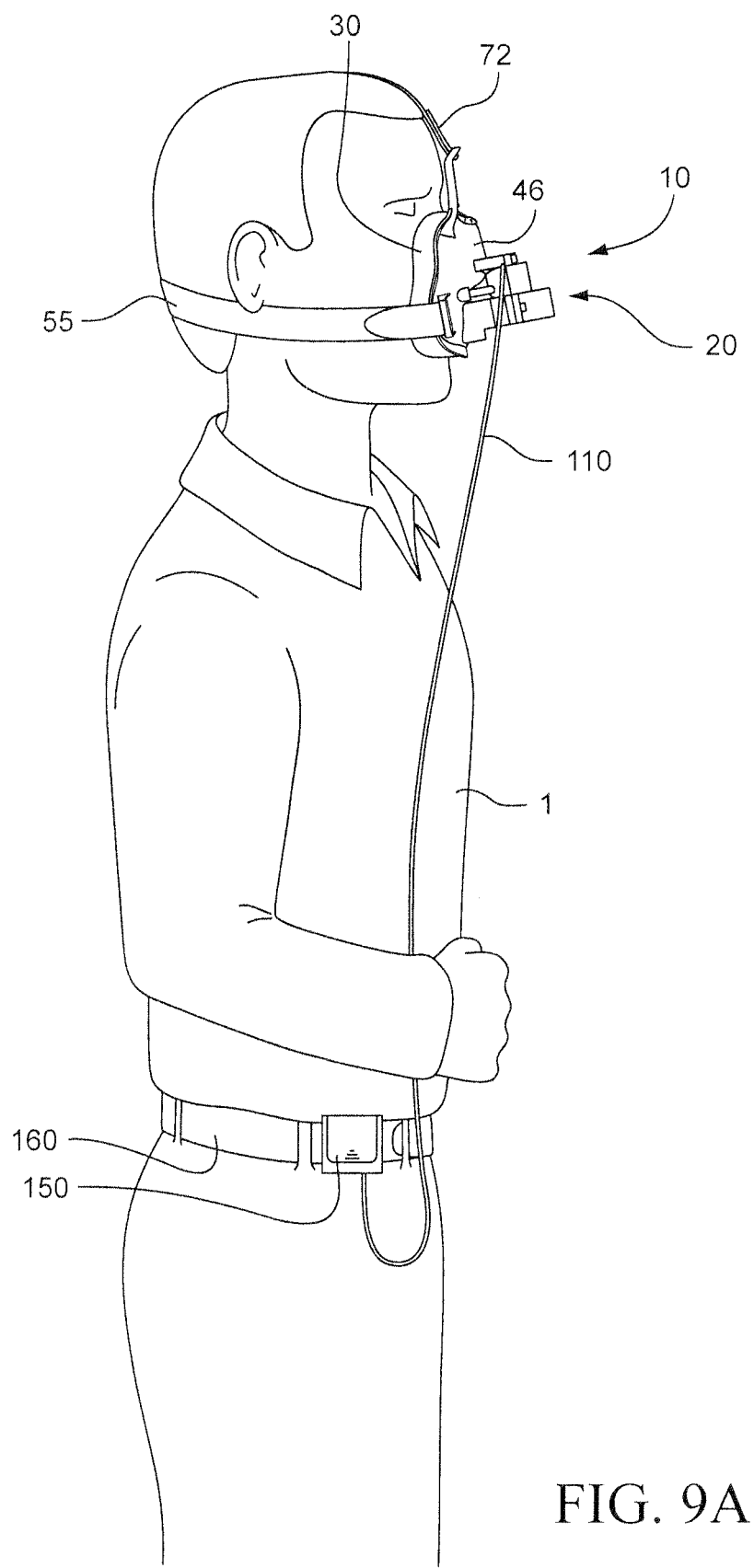
FIG. 9A illustrates a person wearing the CPAP system of FIG. 1.
Figure 9B:
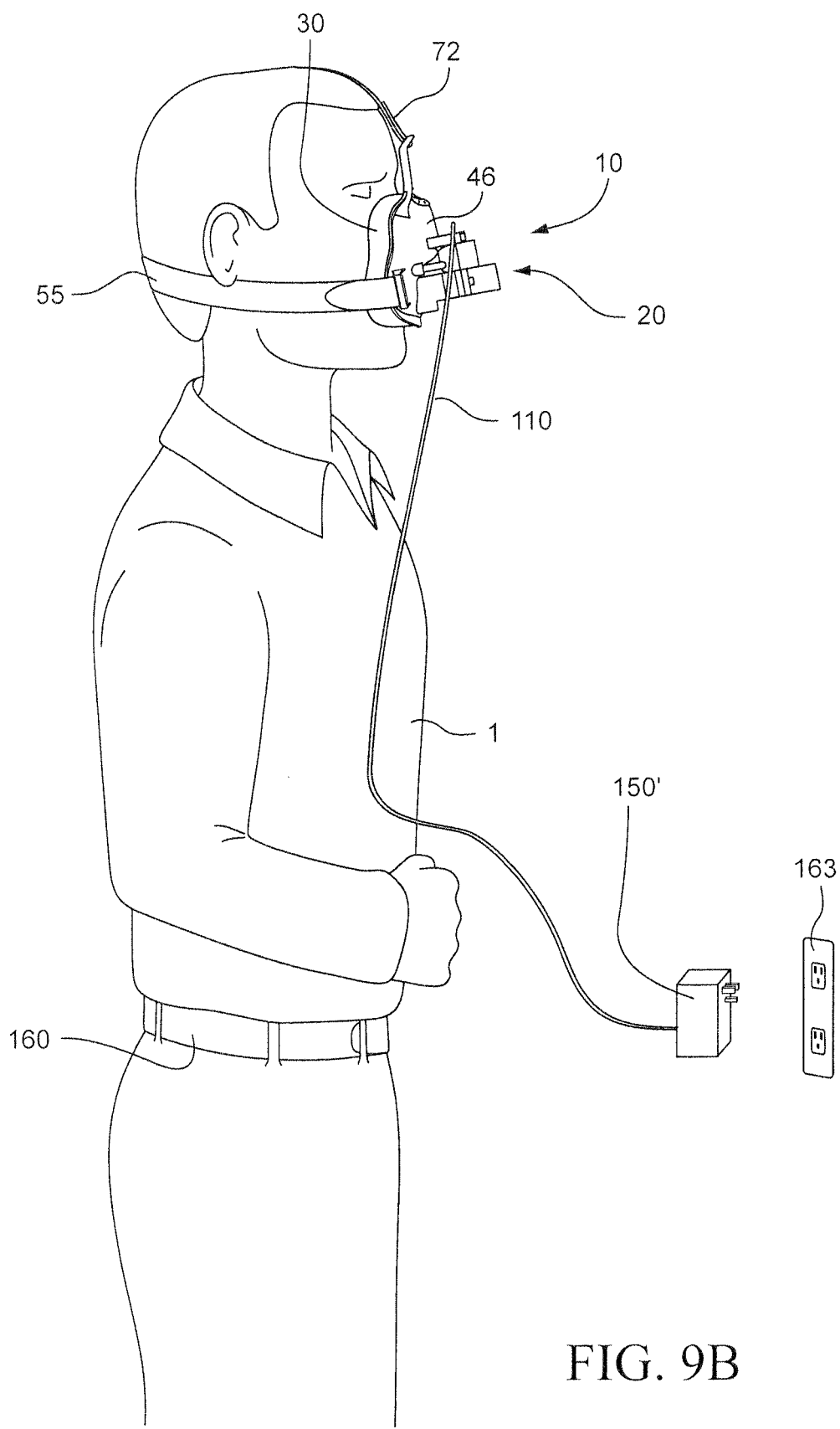
FIG. 9B illustrates an alternative embodiment of the present invention.
Figure 10A:
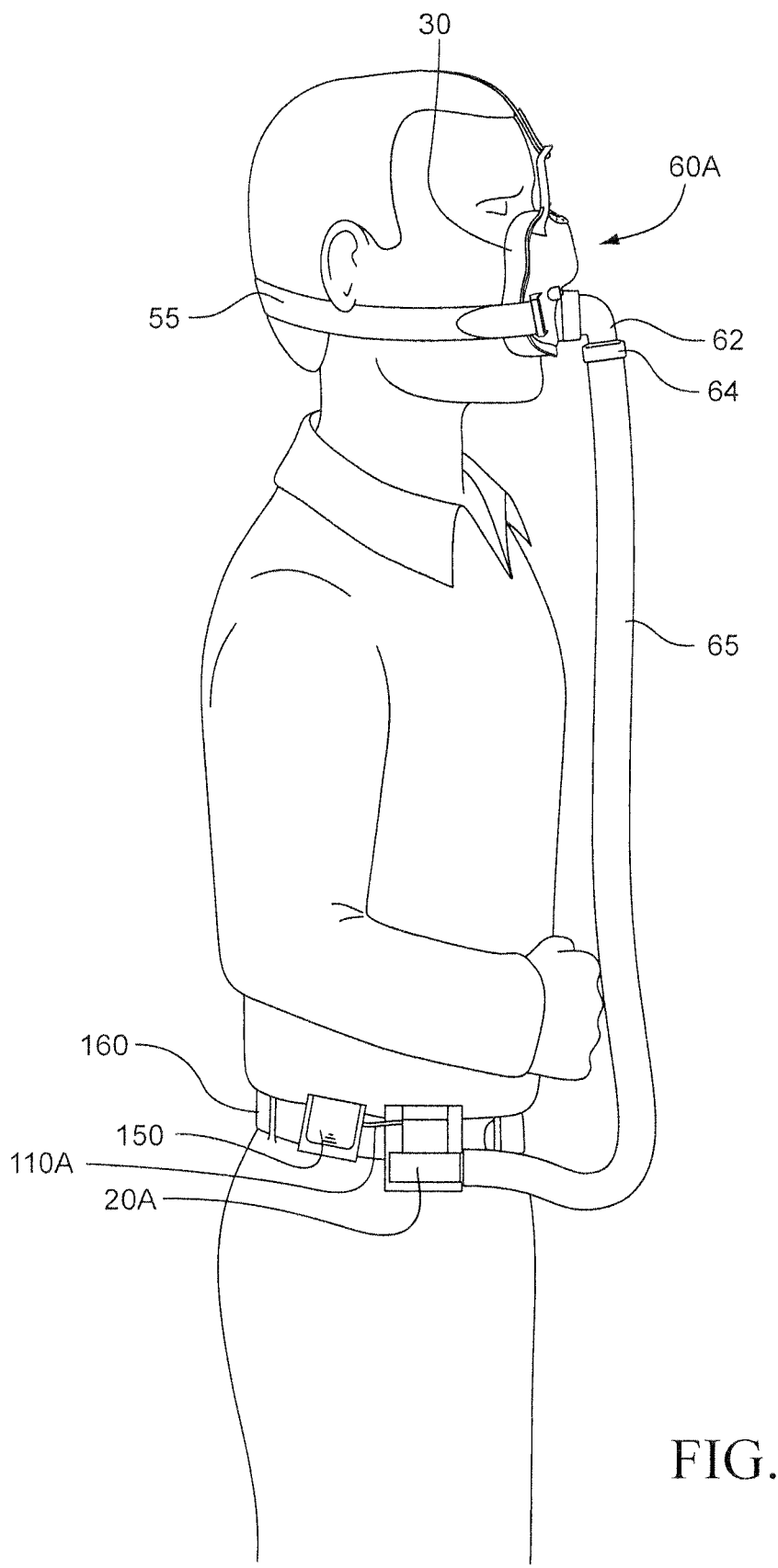
FIG. 10A illustrates a person wearing a CPAP system according to a further embodiment of the invention.

Referring to FIG. 9A, the CPAP system of FIG. 1 is mounted on the face of a wearer 1 by means of strap 55. The power is provided to the air flow generator 20 by battery pack 150 via power cord 110. Battery pack 150 is attached to the wearer's body via strap 160. Advantages of using a battery pack as the power source include, for instance, the increased mobility of the wearer. In yet another embodiment illustrated in FIG. 9B, power to the air flow generator may be provided via a transformer power pack 150' plugged into a wall outlet 163.

FIG. 10A shows an embodiment where impeller system 20A is not directly mounted on mask 60A but instead on a wearer's body via strap 160. The air outlet of air flow generator 20A is attached to air delivery tube 65, which is connected to the air inlet port of full face mask 60A via socket 64 and coupling tube 62. In one embodiment, air delivery tube 65 is shorter than 1.5 meter, for instance 1.0 meter or 0.5 meter. The air delivery tube may be of any diameter or include multiple air tubes that are low profile and/or kink resistant, as described in ResMed's U.S. Patent Application No. 60/494, 119 filed Aug. 12, 2003, incorporated by reference in its entirety. Power is supplied to air flow generator 20A by battery pack 150 via power cord 110A. Power pack or flow generator may also be integrated into one assembly.

Figure 10B:
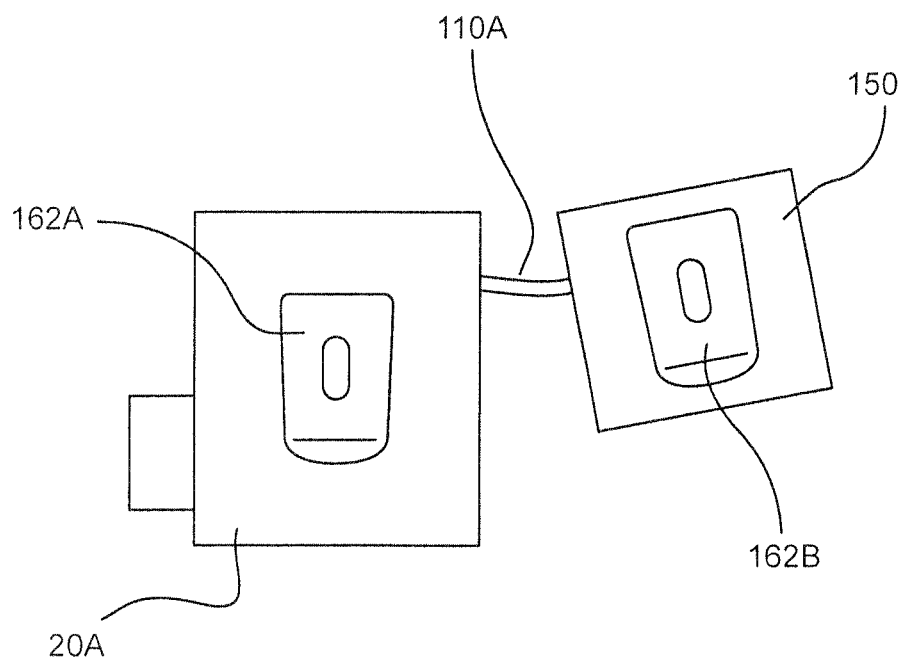
FIG. 10B is a schematic view of an air flow generator and battery pack for a CPAP system according to an embodiment of the invention.
Figure 11A:
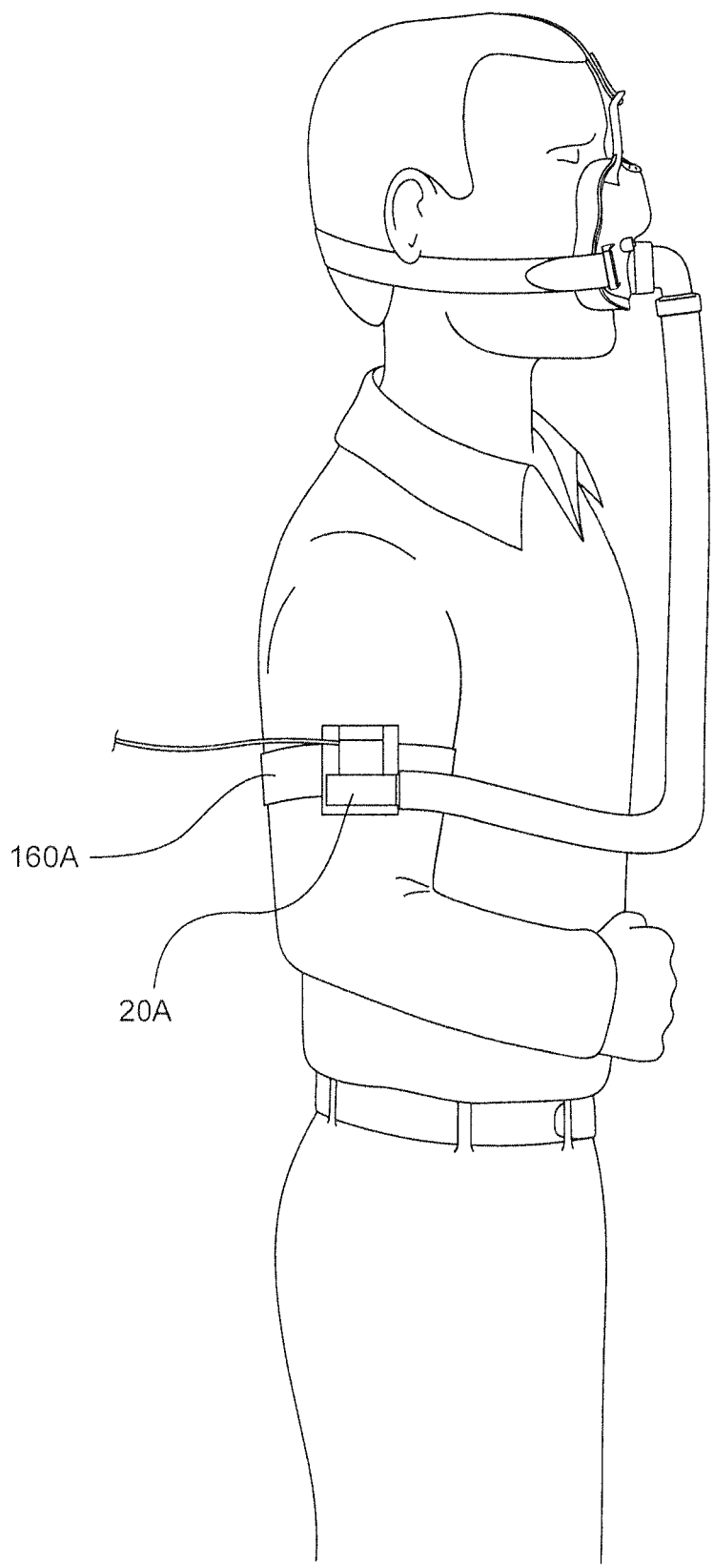
FIG. 11A represents a person wearing a CPAP system according to a further embodiment of the invention.
Figure 11B:
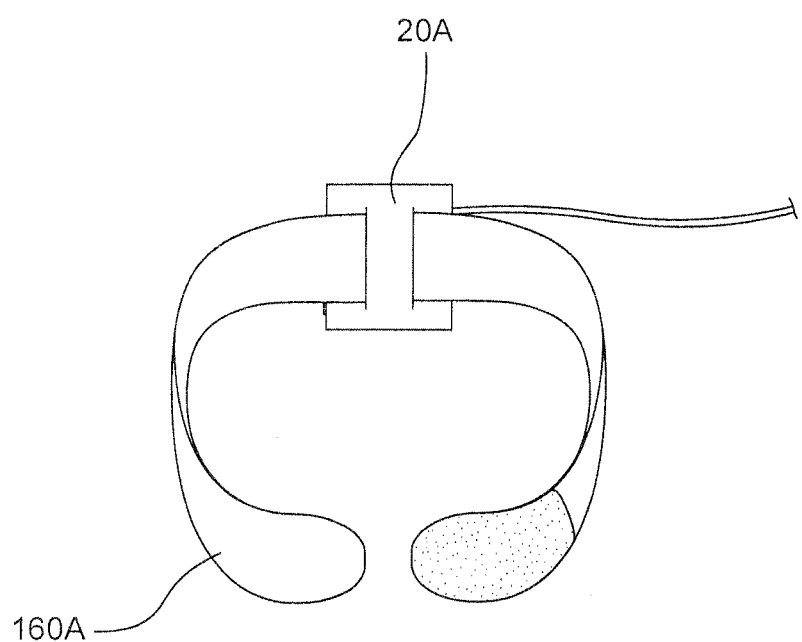
FIG. 11B represents a battery pack and strap for a CPAP system according to an embodiment of the invention.

In one embodiment, air flow generator 20A and battery pack 150 are attached to strap 160 using clips 162A and 162B (see FIG. 10B). Of course, this embodiment is not limited to such an attachment system and the air flow generator and/or battery pack may be attached to any suitable part of a wearer's body (including clothing) by any suitable means. For instance, as depicted in FIGS. 11A and 11B, air flow generator 20A may also be attached to a wearer's arm using, e.g., a Velcro® strap 160A. The motor assembly, including the impeller, may also be attached to other portions of the wearer's body, e.g., the chest via a strap, the shoulder, etc.

Figure 12:
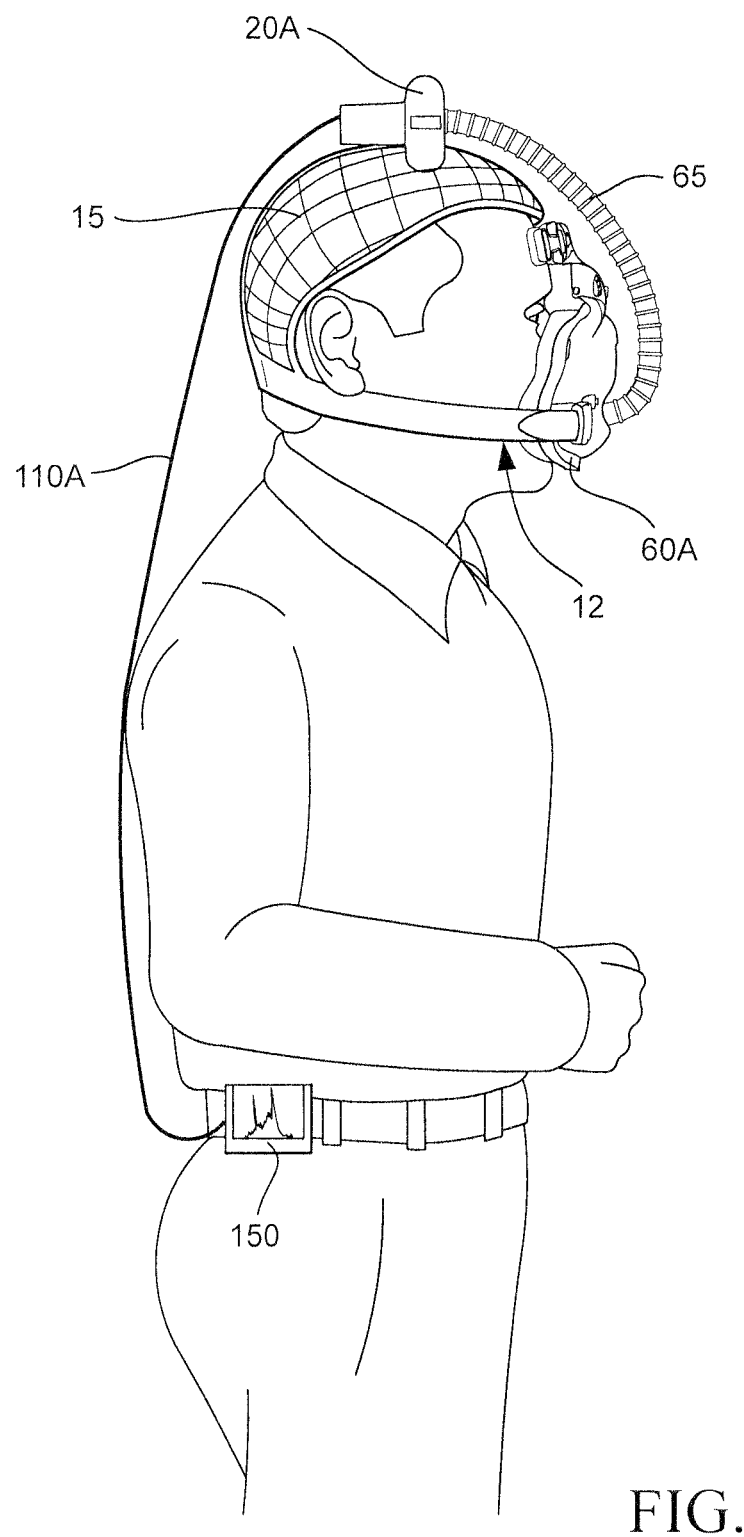
FIG. 12 represents a person wearing a CPAP system according to a further embodiment of the invention.

In yet another variant shown in FIG. 12, the motor assembly 20A may be mounted or provided or combined to a headgear system 12, with short tubing 65 running to the mask 60A. The headgear system 12 could act as form a of vibration damping. Motors invariably vibrate due to imbalances or during motion. Isolating this vibration from the wearer will reduce irritation and noise. As the head is sensitive to vibration, some form of motor and/or impeller isolation is preferable. A damping system may be used; for example a visco-elastic/soft foam "cushion" 15 between the head and flow generator 20A would provide some benefit.

In another aspect, a motor can provide a heat sink to provide ability to warm patient breathing air temperature to improve breathing comfort. An additional aspect is to be able to control the temperature based on ambient conditions, e.g., using a feedback loop. These aspects may be incorporated as part of any of the above embodiments.

While the invention has been described by way of illustrative embodiments, it is understood that the words which have been used herein are words of description, rather than words of limitation. Changes may be made without departing from the scope and spirit of the embodiments. For example, while embodiments have been described as relation to CPAP application, it is to be understood that the features described herein may also have application in the general ventilation or respiratory arts. In addition, the system can be used for children and adults of all ages.

The invention claimed is:

1. A ventilator system configured to provide pressurized air to a patient, the ventilator system comprising:
   a mask having
      a shell;
      a cushion provided to the shell to sealingly connect the mask to a wearer's face and thereby form a chamber between said shell and said wearer's face;
      an inlet port in said shell to receive a flow of breathable gas;
   a flow generator;
   headgear with an airflow generator receiving portion configured to receive the flow generator; and
   an air delivery tube sized to maintain a low profile adjacent the patient's head while fluidly connecting the flow generator to the inlet port, the flow generator being configured to generate a pressure of about 2-40 cm $H_2O$ in the chamber.

2. A ventilator system according to claim 1, wherein the headgear system comprises at least one strap configured to retain the flow generator.

3. A ventilator system according to claim 2, wherein the flow generator comprises a centrifugal, axial or radial fan.

4. A ventilator system according to claim 3, further comprising:
   a damping system configured to reduce vibration and noise transmitted between the flow generator and the patient's head.

5. A ventilator system according to claim 4, wherein the damping system comprises a cushion.

6. A ventilator system according to claim 5, wherein the cushion is made of a visco-elastic foam or soft foam.

7. The ventilator system of claim 1, wherein said air delivery tube does not exceed 1 meter in length.

8. The ventilator system of claim 7, wherein said air delivery tube does not exceed 0.5 meters in length.

9. The ventilator system of claim 8, wherein the air delivery tube is kink resistant.

10. The system of claim 9, wherein the mask and air delivery tube are constructed to avoid obstruction of the wearer's vision.

11. A positive airways pressure system, comprising:
    a patient interface having an inlet port, the patient interface being configured to be placed over and sealingly connected to a wearer's face and the inlet port being configured to receive a pressurised breathable gas;
    headgear configured to secure the patient interface to the wearer's head;
    a motor assembly mounted on or in the headgear; and
    tubing extending from the motor assembly to the inlet port, the tubing being no more than 0.5 meters long,
    wherein the motor assembly is configured to generate a pressure of about 2-40 cm $H_2O$ in the chamber.

12. A positive airways pressure system according to claim 11, further comprising:
    a damping system to reduce vibration and transmitted noise mounted between the flow generator and the wearer's head.

13. A positive airways pressure system according to claim 12, wherein the damping system comprises a cushion.

14. A positive airways pressure system according to claim 13, wherein the cushion is made of a visco-elastic foam or soft foam.

15. A positive airways pressure system according to claim 11, wherein the patient interface is structured to cover the wearer's nasal and oral region.

16. A positive airways pressure system according to claim 15, wherein the patient interface is designed to have said inlet port located in proximity to the wearer's oral region.

17. A positive airways pressure system according to claim 16, wherein said cushion comprises a silicone elastomer.

18. A positive airways pressure system, comprising:
    a face engaging device having a shell and a cushion provided to the shell to sealingly connect the face engaging device to a wearer's face and form a chamber between said shell and said wearer's face;
    a flow generator fluidly connected to the face engaging device and configured to be mounted on the wearer at a first location; and
    a power supply connected to the flow generator and configured to be mounted on the wearer at a second location different from the first location,
    wherein the connection between the flow generator and the face engaging device and the connection between the flow generator and the power supply are configured to be maintained at a low profile against the wearer's body, and
    wherein the flow generator is configured to generate a pressure of about 2-40 cm $H_2O$ in the chamber.

19. A positive airways pressure system according to claim 18, wherein the first location is on the wearer's head and the second location is below the wearer's head.

20. A positive airways pressure system according to claim 19, wherein the connection between the flow generator and the face engaging device comprises kink-resistant tubing, and the connection between the flow generator and the power source comprises a power cord.

21. A positive airways pressure system according to claim 20, wherein said power source is a battery pack.

22. A positive airways pressure system according to claim 21, further comprising:
    a damping system to reduce vibration and transmitted noise mounted between the flow generator and the wearer's head.

23. A positive airways pressure system according to claim 22, wherein the damping system comprises a cushion.

24. A positive airways pressure system according to claim 23, wherein the cushion is made of a visco-elastic foam or soft foam.

25. A positive airways pressure system according to claim 11, wherein the patient interface is a mask.

26. A positive airways pressure system according to claim 18, wherein the face engaging device is a mask.

* * * * *